United States Patent [19]
Kwon et al.

[11] Patent Number: 5,490,512
[45] Date of Patent: Feb. 13, 1996

[54] ELEVATION DIRECTION FOCUSING IN ULTRASOUND TRANSDUCER ARRAYS

[75] Inventors: Seojoong Kwon, Bellevue; Dong-Chyuan Liu, Mercer Island, both of Wash.; Bruce A. McDermott, Chapel Hill, N.C.

[73] Assignee: Siemens Medical Systems, Inc., Iselin, N.J.

[21] Appl. No.: 260,645

[22] Filed: Jun. 16, 1994

[51] Int. Cl.$^6$ .................................................. A61B 8/00
[52] U.S. Cl. .......................................... 128/661.01
[58] Field of Search ..................... 128/660.08, 661.01, 128/660.07; 73/625, 626, 628

[56] References Cited

U.S. PATENT DOCUMENTS

| | | | |
|---|---|---|---|
| 4,550,606 | 11/1985 | Drost | 128/661.01 |
| 5,060,651 | 10/1991 | Kondo et al. | 128/661.01 |
| 5,097,709 | 3/1992 | Masuzawa et al. | 128/661.01 |
| 5,186,175 | 2/1993 | Hirama et al. | 128/661.01 |

*Primary Examiner*—George Manuel

[57] ABSTRACT

Ultrasound imaging apparatus for transmitting ultrasonic signals to a subject to be diagnosed and for reconstructing an ultrasonic diagnostic image from received ultrasonic echo signals, the ultrasound imaging apparatus including: (a) a plurality of transducer elements which are two-dimensionally oriented in an array having a lateral direction and an elevation direction, the transducer elements converting electrical driving signals supplied thereto into the ultrasonic transmitting signals and converting the ultrasonic echo signals into electrical echo signals; (b) apparatus for generating and supplying the electrical driving signals to the transducer elements; (c) apparatus for selectively combining the electrical driving signals and the electrical echo signals sent to or received from transducer elements in the elevation direction; and (d) apparatus for converting the selectively combined electrical echo signals into the ultrasound diagnostic image. In addition, further embodiments further include apparatus for adjusting the levels of the selectively combined electrical driving signals supplied to the transducer elements.

14 Claims, 3 Drawing Sheets

ELEVATION DIRECTION FOCUSING IN ULTRASOUND TRANSDUCER ARRAYS

TECHNICAL FIELD OF THE INVENTION

The present invention relates, in general, to an ultrasound probe and, in particular, to method and apparatus for controlling: (a) transmit and receive elevation apertures and (b) elevation transmit focusing of an ultrasound transducer array.

BACKGROUND OF THE INVENTION

Ultrasound imaging systems have become an important diagnostic tool in many medical specialties. One important advantage of an ultrasound imaging system is real-time scanning. For example, an ultrasound imaging system can produce images so rapidly that a sonographer can scan internal organs or can discern motion within a body, such as blood flow, with real-time, interactive, visual feedback. This allows the sonographer to examine structures of interest and to modify the examination in real-time, thereby speeding and improving the diagnostic process and increasing patient throughput.

Along with the advantages of real-time, interactive, visual feedback, sonographers are still concerned with system resolution. In an ultrasound imaging system, system resolution depends on the system's ability to focus, which ability to focus depends, in turn, on the effective aperture of a transducer array in a probe associated with the ultrasound imaging system. Currently two types of arrangements of transducer array elements are used for real-time, ultrasound imaging systems. One type of arrangement of transducer array elements comprises a single transducer element or an annular array of transducer elements. Ultrasound imaging systems using this type of arrangement of transducer array elements rely on mechanical motion of the probe to sweep an acoustic beam over a region of interest. A second type of arrangement of transducer array elements comprises an array of transducer elements which is activated by electronic circuits which produce electronically induced time delays in the transducer element acoustic outputs, which phase delays cause the acoustic beam produced by the transducer array to be steered and/or focused.

Links between electronic circuits which generate transmit pulses for transducer array elements and the transducer array elements which receive the transmit pulses are referred to as beamformer channels. Electronic steering and/or focusing of an acoustic beam produced by the transducer array is achieved by electronically delaying transmit pulses, on a beamformer channel-by-beamformer channel basis, to create an effective lens having varying thickness. Due to limits on: (a) the size and complexity of a cable connecting the ultrasound probe with the processing system and (b) the number of beamformer channels available in a reasonably priced ultrasound system, electronic focusing has been limited to a lateral direction (a direction parallel to the imaging plane). Focusing in an elevation direction (a direction perpendicular to the imaging plane) has been accomplished by placing a mechanical lens, of fixed curvature, on the probe face. In the prior art, modifications in elevation focusing have been accomplished by changing the probe aperture and/or the mechanical lens. Although it is known that changing frequency can change focal depth (higher frequencies producing deeper focusing than lower frequencies), it is not considered advantageous to change frequency to change focal depth because higher frequencies are attenuated more rapidly in tissue than lower frequencies. Thus, it is known that in order to change elevation focusing of a transducer array, one ought to change the elevation aperture and/or to change the effective lens curvature of the transducer array. For example, in imaging a deep organ, the lens ought to have a large aperture and mild curvature and, in imaging a shallower object, the lens ought to have a smaller aperture and a tighter curvature.

As is known, transducer array elements in an ultrasound probe can be arranged in a 1-D array, a 1.5-D array, or a 2-D array (the size of a typical transducer array element is on the order of 0.5 wavelengths in the lateral direction and is on the order of 50 wavelengths in the elevation direction). In a 1-D array, all transducer elements are disposed in the lateral direction, with a single row of elements in the elevation direction. Conventional phase linear arrays and curved arrays are generally considered to be 1-D arrays. In a 2-D array, transducer elements are mounted in both the lateral and elevation directions, with electrical connections providing control and data to transducer elements in both directions. An acoustic beam produced by a 2-D array can be steered and focused in two dimensions. An example of a 2-D array ultrasound probe can be found in U.S. Pat. No. 5,186,175. In a 1.5-D array, transducer elements are also mounted in both the lateral and elevation directions, but control and data electrical connections are symmetrically connected about the elevation center so that an acoustic beam produced by a 1.5-D array can only be steered in the lateral direction.

The advantages of 2-D array imaging are well known. For example, such advantages include the ability to steer in two (2) dimensions, enhanced resolution due to improved elevation focusing, and improved phase aberration correction through refined comparison of propagation velocities. However, due to the: (a) lack of reliable interconnection technology; (b) limitations on cable size; and (c) limitations on the number of beamformer channels that are commercially viable, 2-D arrays are not considered to be practical yet.

FIG. 1 shows, in pictorial form, a conventional 1.5-D array. The notation N×M describes a transducer array having N lateral transducer elements per row and M transducer elements per column. Further, the notation n*m describes the electrical connections. For example, the 1.5-D array depicted in FIG. 1 is a 64×7 array having 64*4 channels. By grouping transducer elements in the elevation direction into a limited number of groups, and by activating specific ones of the groups when imaging at a specific depth, the 1.5-D array probe is capable of providing some depth dependent focusing in the elevation direction. However, such depth dependent focusing using a 1.5-D array probe suffers from a problem in that switching among the limited number of groups of transducer elements in the elevation direction to change elevation focus causes abrupt textural changes in a displayed image.

In light of the above, there is a need in the art for method and apparatus for controlling elevation focusing of a transducer array of an ultrasound probe by changing the elevation aperture of the transducer array and by smoothly varying elevation focus of transducer arrays having a limited number of transducer array elements in the elevation direction.

SUMMARY OF THE INVENTION

Embodiments of the present invention advantageously satisfy the above-identified need in the art by providing method and apparatus for controlling elevation focusing of a transducer array of an ultrasound probe. In particular, embodiments of the present invention comprise means for changing the elevation aperture of the transducer array electronically and means for smoothly varying elevation focus zones of transducer arrays having a limited number of transducer array elements in the elevation direction.

Specifically, an embodiment of the present invention is an ultrasound imaging apparatus for transmitting ultrasonic signals to a subject to be diagnosed and for reconstructing an ultrasonic diagnostic image from received ultrasonic echo signals, the ultrasound imaging apparatus comprising: (a) a plurality of transducer elements which are two-dimensionally oriented in an array having a lateral direction and an elevation direction, the transducer elements converting electrical driving signals supplied thereto into the ultrasonic transmitting signals and converting the ultrasonic echo signals into electrical echo signals; (b) means for generating and supplying the electrical driving signals to the transducer elements; (c) means for selectively combining the electrical driving signals and the electrical echo signals sent to or received from transducer elements in the elevation direction; and (d) means for converting the selectively combined electrical echo signals into the ultrasound diagnostic image. In addition, further embodiments further comprise means for adjusting the levels of the selectively combined electrical driving signals supplied to the transducer elements.

In a preferred embodiment of the present invention the means for selectively combining, for example, a switching apparatus, and the means for adjusting the levels operate with sufficient speed to enable: (a) aperture size and elevation transmit focus of the transducer array to vary from beam to beam; (b) continuous dynamic receive focusing and aperture growth in the elevation direction; (c) a different set of transducer elements to be used for transmitting an acoustic pulse and for receiving reflections of the acoustic pulse.

In accordance with a further aspect of the present invention, the means for selectively combining enables the transducer array to be configured as a: (a) 1-D array wherein all active rows of transducer elements are summed; (b) 1.5-D array wherein symmetrical transducer elements are summed; or (c) 2-D array wherein adjacent outside transducer elements are summed. Advantageously, in accordance with this aspect of the present invention wherein the means for selectively combining comprises a switching apparatus which combines signals to and from symmetrical or adjacent transducer elements, the number of ultrasound imaging system channels required to perform elevation focusing is reduced.

Advantageously, in accordance with the present invention, the number of elevation elements in a transducer array having a fixed elevation aperture is reduced while still retaining the capability of providing a large number of elevation focal regions. As a result, a single 2-D array can be configured to work in multiple imaging applications which previously would have required a different probe for each application to achieve optimal performance. One 2-D probe should be less expensive than buying multiple 1-D probes, and also produce improved elevation focusing.

DETAILED DESCRIPTION

The present invention solves the problem of achieving control of elevation focusing of a transducer array by two methods and by interaction between the two methods. The first method of achieving control of elevation focusing entails use of electronic switch apparatus for combining inputs and outputs of transducer array elements into predetermined groups to alter the elevation aperture and, thereby, to alter the elevation focus of the transducer array. The second method of achieving control of elevation focusing entails varying transmit voltages applied to elements of a transducer array. We have discovered that the elevation focus of a transducer array can be varied, even while utilizing the same elements, by varying the transmit voltages applied thereto. Finally, in accordance with the present invention, these two methods are utilized in combination to provide smoothly varying elevation focus zones.

Figure 1:
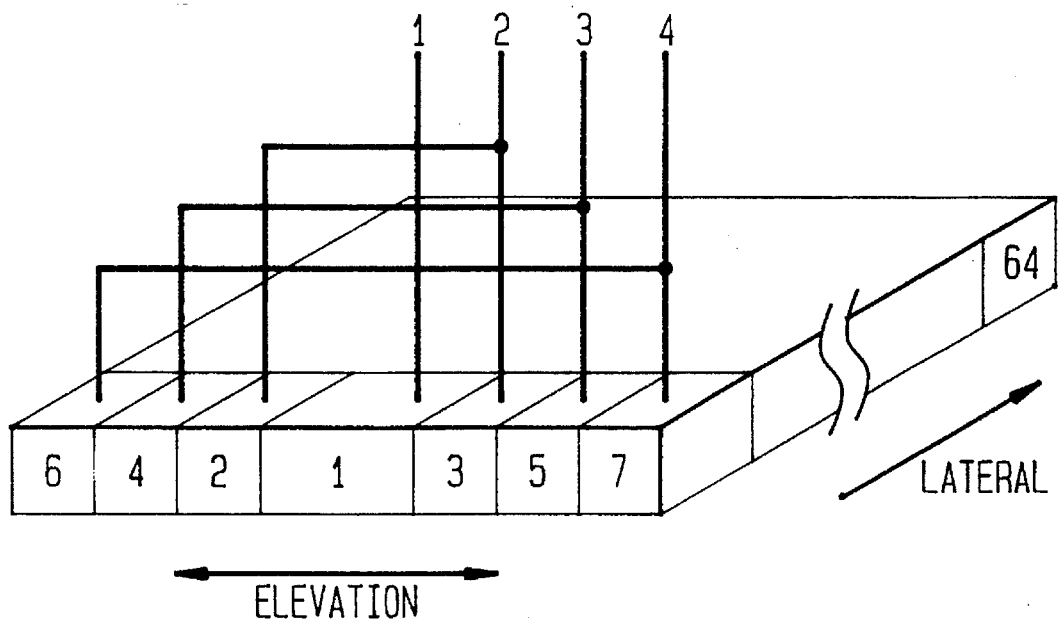
FIG. 1 shows, in pictorial form, a conventional 1.5-D transducer array.
Figure 2:
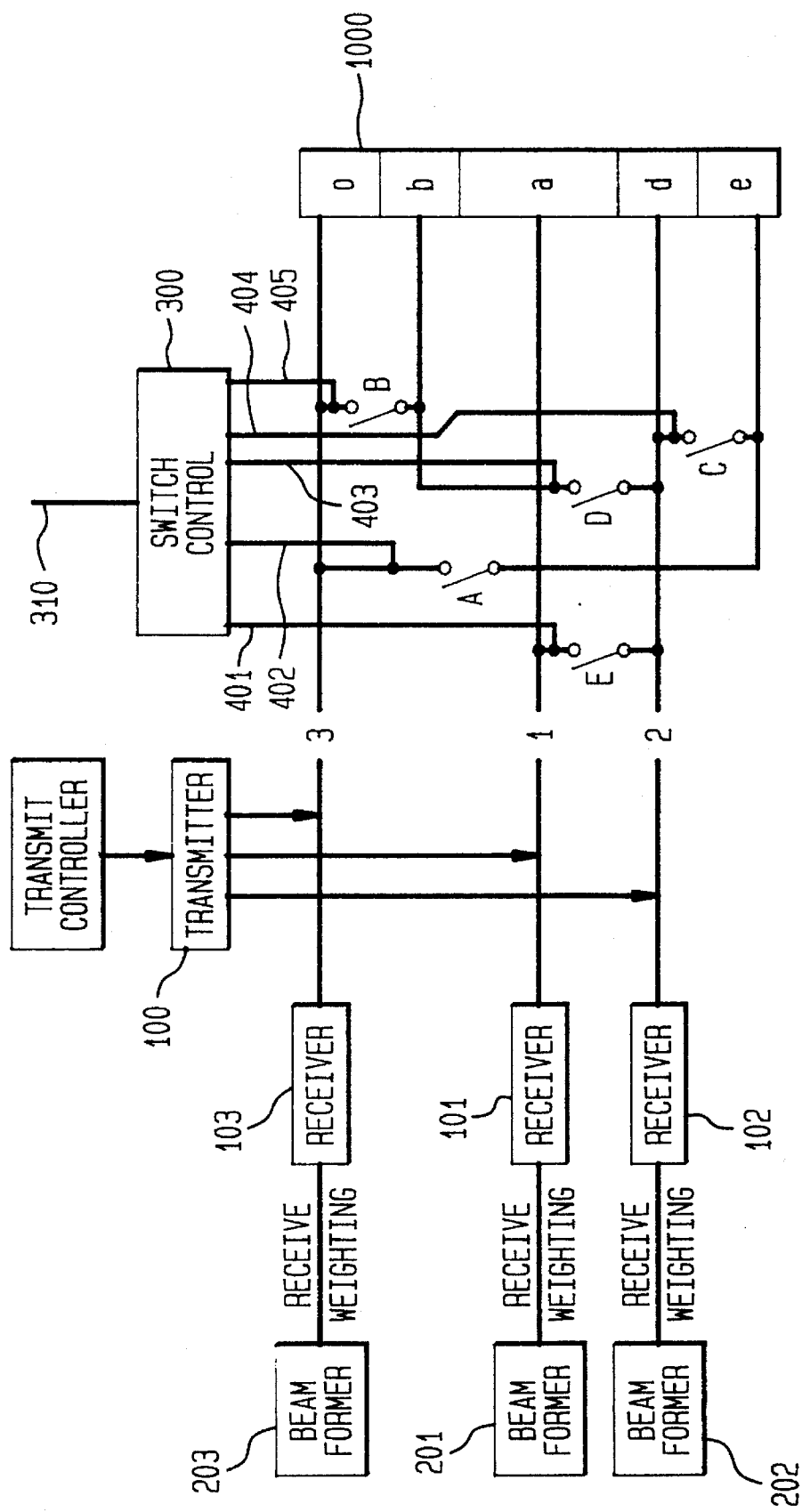
FIG. 2 is a block diagram of a portion of an ultrasound imaging system which illustrates an embodiment of the present invention.

FIG. 2 is a block diagram of a portion of an ultrasound imaging system which illustrates an embodiment of the present invention. As shown in FIG. 2, an embodiment of the present invention includes a switching apparatus comprised of switches (A–E). Transducer array 1000 shown in FIG. 2 merely shows one column in the elevation direction for ease of understanding the present invention. In accordance with the embodiment shown in FIG. 2, the switching apparatus is arranged so that only three beamformer channels (1–3) are utilized to transmit signals to and to receive signals from the six rows of transducer elements (a–e, with two rows in a) of transducer array 1000 in the elevation direction. As a result, for the disclosed embodiment, the number of system channels required is equal to one-half of the number of elements in the transducer array.

As further shown in FIG. 2, transmitter 100 generates and sends electrical signals to channels 1–3 for application to array elements a–e and receivers 101–103 collect electrical signals generated by array elements a–e and send them to beamformers 201–203 for further processing in accordance with methods which are well known to those of ordinary skill in the art. Switch controller 300 opens and closes switches A–E in accordance with the present invention to provide signal paths for selectively activating predetermined elements in transducer array 1000. It should be understood that the present invention is not limited to embodiments wherein: (a) a transducer array is comprised of an even number of transducer elements; (b) one-half as many beamformer channels as there are transducer elements in the elevation direction are utilized; or (c) transducer elements are combined into symmetric groups of elements.

In accordance with the present invention, the aperture of transducer array 1000 can be varied electronically as follows. In accordance with the present invention, in response to signals generated by switch controller 300, switches A–E provide a 1-D array in which all active rows of array elements are summed, a 1.5-D array in which symmetrical array elements are summed, or a 2-D array in which adjacent outside array elements are summed. Advantageously, in accordance with the present invention, when embodiments are configured as either a 1.5-D array or as a 2-D array, the summed array elements have the same capacitance, thereby simplifying tuning requirements. In addition, using switches A–E to connect symmetrical or adjacent elements advantageously reduces the number of ultrasound imaging system channels which are required to perform elevation focusing. Note however, that, in general, the transducer arrays could also be combined into asymmetric groups of transducer elements as well as into symmetric groups of transducer elements.

In accordance with the present invention, switches A–E shown in FIG. 2 are operated to obtain 1-D array, 1.5-D array, or 2-D array operation of transducer array 1000 in accordance with the following. 1-D operation of transducer array 1000 is obtained in a number of ways. Full aperture modes of 1-D array operation of transducer array 1000 are obtained by: (i) closing switches A–E or (ii) closing switches B, C, D, and E. Such full aperture modes would utilize beamformer channel 1. Less than full aperture modes of 1-D array operation of transducer array 1000 are obtained by: (i) opening all switches A–E (a narrow aperture spanned by element a) or (ii) closing switches D and E and opening switches A, B, and C (art aperture spanned by elements a, b, and d). Such less-than-full aperture modes would again utilize beamformer channel 1.

1.5-D array operation of transducer array 1000 is obtained by: (1) closing switch D and opening switches A, B, C, and E (an aperture spanned by elements a, b, and d wherein transducer element a is addressed by beamformer channel 1 and elements b and d are addressed by beamformer channel 2) and (2) closing switches A and D and opening switches B, C, and E(an aperture spanned by elements a–e wherein transducer element a is addressed by beamformer channel 1, transducer elements b and d are addressed by beamformer channel 2, and transducer elements c and e are addressed by beamformer channel 3). Lastly, 2-D array operation of transducer array 1000 is obtained by closing switches B and C and opening switches A, D, and E ((an aperture spanned by elements a–e wherein transducer element a is addressed by beamformer channel 1, transducer elements d and e are addressed by beamformer channel 2, and transducer elements b and c are addressed by beamformer channel 3).

The manner in which switch controller 300 operates to open and close switches A–E is well known to those of ordinary skill in the art. For example, switch controller 300 may be fabricated as a microprocessor controlled apparatus for receiving information from the ultrasound control system (not shown) over communications link 310 and for sending signals to switches A–E in conventional manner. As is well known, switch controller 300 may also be fabricated from dedicated programmable logic array devices. As has been described above, after the mode of operation (for example, 1-D array, 1.5-D array, or 2-D array and the particular aperture to utilize) has been transmitted to switch controller 300 from the ultrasound control system, switch controller 300 converts that information into an appropriate set of signals for transmission to switches A–E over leads 401–405 to control operation thereof. In a preferred embodiment of the present invention, communications link 310 is disposed in the cable which connects the ultrasound probe to the rest of the system and which cable also carries beamformer channels 1–3. Switches A–E are fabricated from high voltage (on the order of 100 V), high speed switches which are operated by relatively low currents. Switches of this type are commercially available from, for example, AT&T.

In accordance with a preferred embodiment of the present invention, switch controller 300 and switches A–E provide a switching function that is sufficiently rapid so that, in response to information received over communications link 310 from the ultrasound control system, a first set of transducer elements can be used to transmit an ultrasound acoustic pulse and another set of transducer elements can be used to receive reflections of that pulse.

It should be noted that it is considered advantageous to utilize embodiments of the present invention to provide 2-D array operation of transducer array 1000 when employing a phase aberration correction application rather than 1.5-D array operation of transducer array 1000. The reason it is considered advantageous to provide 2-D array operation is that: (a) 2-D array operation, as described above, sums signals from adjacent array elements whereas 1.5-D operation, as described above, sums signals from symmetrical array elements and (b) non-adjacent array elements could be subject to dissimilar phase aberrations when phase aberration correction is applied in both lateral and elevation dimensions.

In accordance with the present invention, the ultrasound imaging system can independently control elevation focus by applying separate voltage levels to individual transducer array elements in elevation. This achieves variation in focus by applying a signal to the transducer array which has an amplitude shape across the transducer array in the elevation direction which alters the effective array aperture. For example, the array aperture may be reduced effectively by reducing the voltage levels applied to outer elements of the array. In fact, the acoustic focal regions of the ultrasound probe can be changed continuously by adjusting the transmit voltage level which is applied to appropriately connected array elements in the elevation dimension of a two dimensional array of ultrasound transducers.

Figure 3:
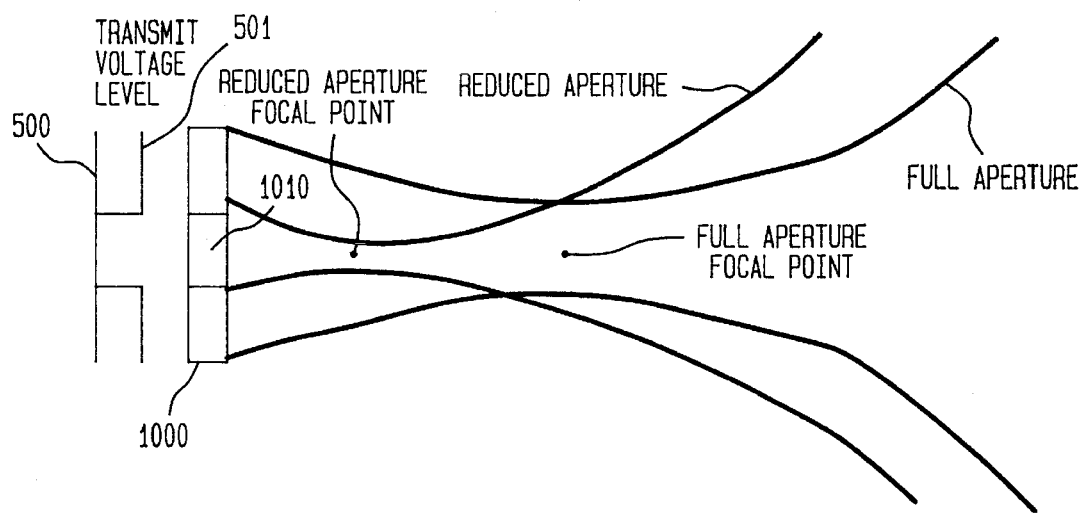
FIG. 3 shows, in pictorial form, focal points for a full elevation aperture and for a reduced elevation aperture produced in accordance with the present invention wherein the same transmit voltage level is applied to each transducer array element in the aperture.

FIG. 3 shows, in pictorial form, focal points for a full elevation aperture and for a reduced elevation aperture produced in accordance with the present invention wherein the same transmit voltage level is applied to each transducer array element in the aperture. Signal 500 comprises a uniform voltage level that is applied to each element of transducer array 1000 to produce a full aperture beam and a full aperture focal point shown in FIG. 3. Signal 501 comprises a uniform voltage level that is applied to each element in sub-array 1010 and a zero voltage level that is applied to other elements of array 1000 to produce a reduced aperture beam and a reduced aperture focal point shown in FIG. 3. As shown in FIG. 3, a shallower elevation focal range is provided with the reduced elevation aperture.

Figure 4:
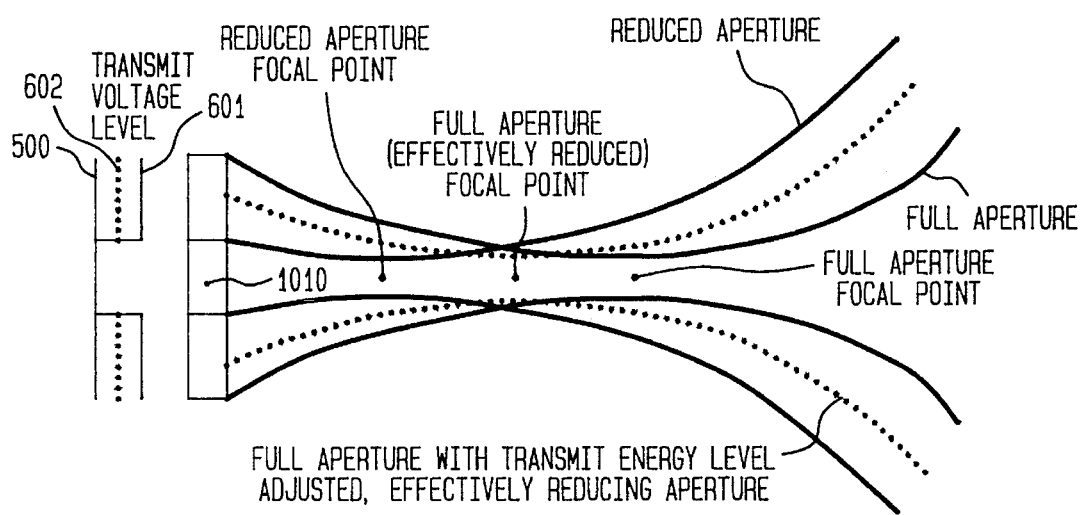
FIG. 4 shows, in pictorial form, focal points for a full elevation aperture, for a reduced elevation aperture, and for an intermediate aperture produced in accordance with the present invention wherein different transmit voltage levels are applied to transducer array elements.

FIG. 4 shows, in pictorial form, focal points for a full elevation aperture, for a reduced elevation aperture, and for an intermediate aperture produced in accordance with the present invention wherein different transmit voltage levels are applied to transducer array elements. This illustrates how transmit voltage level may be varied to change the effective focal point of the transducer array. Signal 600 comprises a uniform voltage level that is applied to each element of transducer array 1000 to produce a full aperture beam and a full aperture focal point shown in FIG. 4. Signal 601 comprises a uniform voltage level that is applied to each element in sub-array 1010 and a zero voltage level that is applied to other elements of array 1000 to produce a reduced aperture beam and a reduced aperture focal point shown in FIG. 4. Finally, signal 602 comprises a uniform voltage level that is applied to each element in sub-array 1010 and a reduced voltage level that is applied to other, outer elements of array 1000 to produce an effectively reduced focal point, full aperture beam and adjusted focal point shown in FIG. 4. Thus, the full aperture focal point that is effectively reduced is located between the full aperture focal point and the reduce aperture focal point. Hence, in general, by applying an appropriate transmit voltage to selected elements in the elevation direction (effectively applying apodization coefficients to each transmit and receive signal) one can adjust the effective aperture in the elevation direction. In this way, the number of elevation elements in a probe with fixed elevation aperture is reduced while maintaining a large number of elevation focal regions. Since the number of elements is proportional to the number of beamformer channels, the smaller the number of desired elevation elements, the lower the cost of manufacturing the system and the effort of making the probe.

Although various minor modifications may be suggested by those versed in the art, it should be understood that we wish to embody within the scope of the patent granted hereon all such modification as reasonably and properly come within the scope of our contribution to the art.

What is claimed is:

1. An ultrasonic imaging apparatus for transmitting ultrasonic signals to a subject to be diagnosed and for reconstructing an ultrasonic diagnostic image from received ultrasonic echo signals, the ultrasound imaging apparatus comprising:

a plurality of transducer elements two-dimensionally oriented to define multiple rows and multiple columns of transducer elements, transducer elements oriented along a lateral direction to define the multiple rows, transducer elements oriented along the elevation direction to define the multiple columns, the transducer elements converting electrical driving signals supplied thereto into ultrasonic transmitting signals and converting the ultrasonic echo signals into electrical echo signals;

means for generating a first electrical driving signal and a second electronic driving signal, the first and second electrical driving signal having differing voltage levels; and means for selectively coupling the first electrical driving signal to a first one or more transducer elements in a first column and the second electrical driving signal to a second one or more transducer elements in the first column, the first one or more transducer elements and second one or more transducer elements being mutually exclusive.

2. The ultrasound apparatus of claim 1 which further comprises means for adjusting voltage levels of the first electrical driving signal and the second electrical driving signal to focus the ultrasonic transmitting signals along the elevation.

3. The ultrasound apparatus of claim 2 wherein the means for adjusting comprises means for selecting among a plurality of voltage levels.

4. The ultrasound apparatus of claim 1, wherein the means for selectively coupling comprises a plurality of switches.

5. The ultrasound apparatus of claim 4, wherein the means for selectively coupling is for coupling a plurality of electrical driving signals having differing voltage levels, said plurality of electrical driving signals comprising the first electrical driving signal and the second electrical driving signal, said plurality of electrical driving signals comprising fewer differing voltage levels than the number of transducer elements in the elevation direction.

6. The ultrasound apparatus of claim 1, wherein the means for selectively coupling comprises means for defining a 1.5-D array.

7. The ultrasound apparatus of claim 1, wherein the means for selectively coupling comprises means for defining a 2-D array.

8. A method of focusing an ultrasound transducer array along an elevation direction in an ultrasound imaging apparatus, the array comprising the method comprising the steps of:

selecting a plurality of first groups of one or more rows of transducer elements to define a transmit elevation aperture;

receiving electronic driving signals at the transducer elements which define the transmit elevation aperture;

outputting ultrasonic transmitting signals at the transducer elements which define the transmit elevation aperture;

selecting a plurality of second groups of one or more of rows of transducer elements to define a receive elevation aperture;

receiving the ultrasonic echo signals at the transducer elements which define the receive elevation aperture; and focusing the output ultrasonic transmitting signals along the elevation at a target depth without use of a mechanical acoustic lens device by receiving different voltage levels of the electronic driving signals at a first one and a second one of the plurality of first groups and by selectively defining the plurality of first groups and the plurality of second groups.

9. The method of claim 6, in which the step of focusing comprises changing the voltage levels to alter a focal plane of the transmitted ultrasonic signals in the elevation direction.

10. The method of claim 9 in which the receive elevation aperture differs from the transmit elevation aperture.

11. The method of claim 8, in which the step of selecting the plurality of first groups comprises the step of electrically defining switch positions for electrically coupling one or more rows to define a respective one group of the plurality of first groups.

12. The method of claim 8, in which the plurality of first groups and the plurality of second groups define a 1.5-D array.

13. The method of claim 8, in which the plurality of first groups and the plurality of second groups define a 2-D array.

14. An ultrasound imaging apparatus for transmitting ultrasonic signals to a subject to be diagnosed and for reconstructing an ultrasonic diagnostic image from received ultrasonic echo signals, the ultrasound imaging apparatus comprising:

a plurality of transducer elements which are two-dimensionally oriented in an array having a lateral direction and an elevation direction, the transducer elements converting electrical driving signals supplied thereto into the ultrasonic transmitting signals and converting the ultrasonic echo signals into electrical echo signals;

means for generating and supplying the electrical driving signals to the transducer elements, wherein the voltage levels of the electrical driving signals are adjustable to differ among transducer elements along the elevation direction; and means for converting the electrical echo signals into the ultrasound diagnostic image.

* * * * *